US010329551B2

(12) United States Patent
Caiafa et al.

(10) Patent No.: US 10,329,551 B2
(45) Date of Patent: *Jun. 25, 2019

(54) ELECTRIC PULSE GENERATION SYSTEMS USING CAPACITIVE COUPLING

(71) Applicant: General Electric Company, Schenectady, NY (US)

(72) Inventors: Antonio Caiafa, Albany, NY (US); Vasile Bogdan Neculaes, Niskayuna, NY (US); Allen Lawrence Garner, West Layfayette, IN (US); Andrew Soliz Torres, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/651,900

(22) Filed: Jul. 17, 2017

(65) Prior Publication Data

US 2017/0314009 A1    Nov. 2, 2017

Related U.S. Application Data

(63) Continuation of application No. 14/158,106, filed on Jan. 17, 2014, now Pat. No. 9,708,597.

(51) Int. Cl.
| | | |
|---|---|---|
| *H03K 3/017* | (2006.01) | |
| *C12N 13/00* | (2006.01) | |
| *A61B 5/15* | (2006.01) | |
| *H03K 3/53* | (2006.01) | |
| *C12M 1/42* | (2006.01) | |
| *G01N 33/49* | (2006.01) | |

(52) U.S. Cl.
CPC ........ *C12N 13/00* (2013.01); *A61B 5/150755* (2013.01); *C12M 35/02* (2013.01); *G01N 33/49* (2013.01); *H03K 3/53* (2013.01)

(58) Field of Classification Search
CPC ........ C12N 9/0006; C12N 9/16; C12N 15/79; C12P 7/6463
See application file for complete search history.

(56) References Cited

U.S. PATENT DOCUMENTS

| | | | |
|---|---|---|---|
| 5,186,800 A | | 2/1993 | Dower |
| 6,010,613 A | * | 1/2000 | Walters ................. C12M 35/02 205/701 |

(Continued)

FOREIGN PATENT DOCUMENTS

WO    2005/032646 A2    4/2005

OTHER PUBLICATIONS

Freitag, Julian et al.; "Photoactivated platelet-rich plasma therapy for a traumatic knee chondral lesion", BMJ Case Reports 2012: doi 10.1136/bcr-2012-006858 (abstract only).

(Continued)

*Primary Examiner* — Sibin Chen
(74) *Attorney, Agent, or Firm* — Fletcher Yoder, P.C.

(57) ABSTRACT

In accordance with the present disclosure, exposure of a sample to one or more electric pulses via capacitive coupling is described. In certain embodiments, the sample may be a biological sample to be treated or modified using the pulsed electric fields. In certain embodiments, the electric pulses may be delivered to a load using capacitive coupling. In other embodiments, the electric pulses may be bipolar pulses.

17 Claims, 4 Drawing Sheets

(56) References Cited

U.S. PATENT DOCUMENTS

| | | | |
|---|---|---|---|
| 6,326,177 | B1 | 12/2001 | Schoenbach et al. |
| 7,565,201 | B2 | 7/2009 | Blackmore et al. |
| 9,078,862 | B2 | 7/2015 | Neculaes et al. |
| 9,238,808 | B2 | 1/2016 | Caiafa et al. |
| 2009/0212788 | A1 | 8/2009 | Patterson |
| 2011/0259091 | A1* | 10/2011 | Laubscher ............. B01L 3/545 73/64.56 |

OTHER PUBLICATIONS

AdiStem PhotoActivated PRP & Stem Cell Technology website downloaded 2014: http://www.adistem.com/technology/prp/.

French, D. M., et al., "Conductive versus capacitive coupling for cell electroporation with nanosecond pulses," Journal of Applied Physics, vol. 106, Issue No. 7, pp. 1-4 (Oct. 8, 2009).

Laplante, N., et al., "Ex-vivo platelet activation using electric pulse stimulation," International Conference on Biomedical Electronics and Devices, pp. 202-208 (Feb. 11, 2013).

Office Action issued in connection with corresponding EP Application No. 14815988.2 dated Jul. 26, 2017.

\* cited by examiner

ELECTRIC PULSE GENERATION SYSTEMS USING CAPACITIVE COUPLING

CROSS-REFERENCE TO RELATED APPLICATIONS

This application is a continuation of U.S. patent application Ser. No. 14/158,106 entitled "ELECTRIC PULSE GENERATION SYSTEMS USING CAPACITIVE COUPLING," filed on Jan. 17, 2014, which is incorporated by reference herein in its entirety for all purposes.

BACKGROUND

The subject matter described herein relates generally to applications utilizing electrical stimulation in the form of pulses, such as in cell therapy and other medical contexts.

Pulsed power has numerous industrial applications, such as medical treatments, biotechnology, food processing, water treatment (e.g., water purification), exhaust gas treatment, ozone generation, and ion implantation. For example, transfection is a medical technique used to permeabilize cell membranes to facilitate DNA plasmid entry into the cell. This technique, also known as electroporation, typically involves applying electric pulses with sufficient strength and duration to permeabilize the cell membrane while maintaining viability. Once the cell membrane is rendered "leaky," DNA in a surrounding buffer solution passes into the cell. Certain in vivo and ex vivo platelet activation methods also utilize pulsed electrical stimulation.

Oftentimes in medical techniques employing pulsed power, the pulse generation system is directly coupled to the container (e.g., a cuvette) that holds the sample being stimulated. In a directly (i.e., conductively) coupled system, the current associated with the electric pulse flows directly through the sample. Typical square wave pulses are utilized for electroporation, where one could adjust the pulse width, the pulse amplitude, number of pulses and the frequency. This may require special containers made of a conductive material (i.e., metal), which may be expensive or which may not be suitable for biological or biochemical specimens.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, an electric pulse generation system includes memory, a display, and a user input device. The pulse generation system also includes a sample holder which includes a first and second electrode disposed on either side of a container containing a sample. The pulse generation system includes pulse generating circuitry configured to supply a pulse to the first and second electrodes, and a capacitive element disposed between the pulse generating circuitry and the second electrode. The pulse generating circuitry is capacitively coupled to the container. The pulse generation system also includes a processor configured to execute instructions stored on the memory to control the pulse generating circuitry.

In a second embodiment, an electric pulse generation system includes a memory, a display, and a user input device. The pulse generation system also includes a sample holder that includes a first and second electrode disposed on either side of a container containing a sample. The pulse generation system includes pulse generating circuitry configured to supply a pulse to the first and second electrodes, and a capacitive element disposed between the pulse generating circuitry and the second electrode. The capacitive element may be removable or may be bypassed during operation of the electric pulse generation system. The pulse generation system also includes a processor configured to execute instructions stored on the memory to control the pulse generating circuitry and whether the pulse generating circuitry is directly or capacitively coupled to the sample.

In a third embodiment, a method includes collecting blood from a patient. A configuration of a sequence of one or more electric pulses is specified based on a desired parameter associated with growth factor release. The blood sample or a platelet rich plasma sample derived from the blood sample is then exposed to the sequence of one or more pulsed electric fields via a capacitively coupled pulse generation system to trigger release of a growth factor in the blood sample or the platelet rich plasma.

In a fourth embodiment, an electric pulse generation system may include a memory, a display, and a user input device. The electric pulse generation system may also comprise a sample holder including a first electrode and a second electrode disposed on opposite sides of the sample holder, wherein the sample holder is configured to receive a sample container and pulse generating circuitry configured to supply a first pulse and a second pulse to the first and second electrodes. The first pulse has a pulse duration and a first electric field strength and the second pulse has the pulse duration and a second electric field strength. The first electric field strength and the second electric field strength are additive inverses. The electric pulse generation system may further include a processor configured to execute instruction stored on the memory to control the pulse generating circuitry.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Present embodiments relate to a pulse generation system for applications employing pulsed power. Specifically, the embodiments described herein relate to a pulse generation system used for medical applications wherein the load may be a biological sample placed in a cuvette or other suitable vessel. The pulse generation system may be coupled to the corresponding load by capacitive coupling, and in some embodiments, by both capacitive and direct coupling. If the load may be coupled to the pulse generation system by both capacitive and direct coupling, an operator may select which type of coupling to use. Although the embodiments described herein relate to a specific medical application, it should be appreciated that these are merely examples of possible uses of the subject matter. Accordingly, the disclosed techniques may be implemented, for example, in other medical treatment applications, biotechnology, food processing, water treatment (e.g., water purification), exhaust gas treatment, ozone generation, and ion implantation. In particular, the samples exposed to the electric pulses may be samples used in medical treatment, biotechnology, food processing, water treatment (e.g., water purification), exhaust gas treatment, ozone generation, and/or ion implantation techniques.

Figure 1:
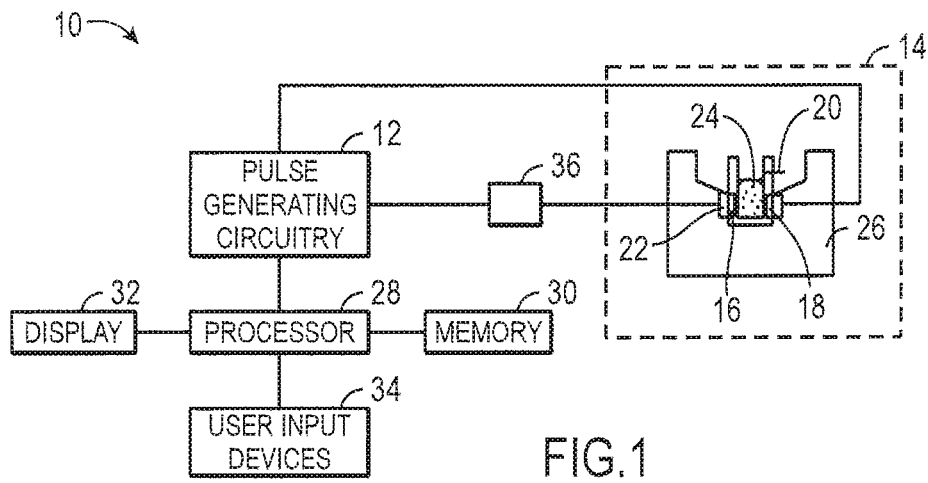
FIG. 1 is a schematic of a capacitively coupled pulse generation system and load, in accordance with an embodiment of the present approach.

With the foregoing in mind, FIG. 1 illustrates a pulse generation system 10. The pulse generation system 10 may include pulse generating circuitry 12 and a load 14. The load 14 may include electrode sets (or array of electrodes) 16 and 18; the electrodes 16 and 18 may be designed to conduct high amounts of current, such as in the range of 0.01-35 kA. In the depicted embodiment, the electrodes 16 and 18 are spaced apart on opposite sides of a cuvette 20. That is, the cuvette 20 is disposed between and contacted by the electrodes 16 and 18 and the electrodes are coupled to the pulse generator via contacts 22. In one embodiment, the cuvette 20 is configured to hold a biological or biochemical sample 24, such as a blood sample. In certain embodiments, the cuvette 20 is disposable and/or is removable from a sample holder 26. Accordingly, insertion of the cuvette 20 and contact of the electrodes 16 and 18 with the contacts 22 allows the pulse generator to produce an electric pulse, and the sample 24 within the cuvette 20 is exposed to the pulses. Although the illustrated embodiment depicts a cuvette 20, it should be appreciated that a cuvette is but one example of a sample container, and that any suitable container configured to hold a sample may be disposed between the electrodes 16 and 18. In certain embodiments, the cuvette 20 or the corresponding sample holder may conduct the electric pulses. The cuvette 20 separates the electrodes 16 and 18 from one another. Though the preceding description describes the cuvette holding a biological sample, it should be appreciated that the load 14 may include any suitable sample that benefits from exposure to electric pulses and the corresponding sample holder.

In certain embodiments, the system 10 may include suitable control and input circuitry and may be implemented in a dedicated housing or may be coupled to a computer or other processor-based system. The system 10 may include a processor 28 that controls the pulse generating circuitry 12. Additional components of the system 10 may include a memory 30 storing instructions executed by the processor 28. Such instructions may include protocols and/or parameters for the electric pulses generated by the pulse generating circuitry 12. The processor 28 may include, for example, general-purpose single-or multi-chip microprocessors. In addition, the processor 28 may be any conventional special purpose processor, such as an application-specific processor or circuitry. The memory 30 may be a mass storage device, a FLASH memory device, removable memory, etc. In addition, a display 32 may provide indications to an operator related to the operation of the system 10. The system 10 may include a user input device 34 (e.g., a keyboard, mouse, touchscreen, trackball, hand held device or controller or any combination thereof) for activating the pulse generating circuitry 12 and/or selecting appropriate parameters.

In the depicted embodiment, the system 10 is used for ex vivo platelet activation. For example, the sample may be a blood product that has been removed from the body and processed to enrich the platelet concentration (e.g., platelet rich plasma). In other embodiments, the system 10 may be used for in vivo techniques. Accordingly, the system 10 may be implemented as a wand or other handheld device with spaced electrodes that delivers an electric pulse in or on a load.

It is envisioned that the pulse generation system 10 as provided herein may be implemented as a single-purpose device (e.g., solely for platelet activation) or as a multi-purpose device that may be used for other electric field exposure applications, such as electroporation, in addition to platelet activation, as discussed herein. Further, the system 10 may be configured to generate an electric pulse according to one or more protocols. The protocols may be generated by user inputs and/or may be stored in the memory 30 to be selected by the user. In one embodiment, the system 10 may operate without any user input to the activation protocol other than an input to start activation once the sample 24 is loaded. In such an embodiment, the pulse generating circuitry 12 may operate under control of the processor 28 to operate a single protocol with predetermined electric field strength, pulse length, and/or total exposure time. Such a protocol may be determined by empirical or theoretical studies. In other embodiments, the system 10 may be configured to receive a user input related to the electric field strength, pulse length, and/or total exposure time. Further, the system 10 may be configured to generate a particular pulse shape or to generate a series of pulses that may differ from one another according to a user input and/or a stored protocol setting.

The pulses generated by the system 10 may have a duration from about 1 nanosecond to about 100 microseconds, and an electric field strength from about 0.1 kV/cm to 350 kV/cm, depending on the application. The spacing between the electrodes 16 and 18 may influence the strength of the electric field, which is defined as the ratio of the applied voltage and the electrode gap distance. For example, if a cuvette provides a 1 cm gap between the electrodes, exposing the cuvette to 1 kV yields an electric field strength of 1 kV/cm. While the pulses generated by the system may be at least 10 kV/cm, 50 kV/cm, etc., they should not exceed the breakdown field of the sample 24.

In conventional systems, a pulse generation system would be directly coupled to the corresponding load, such that current would flow directly from the pulse generating circuitry to and through the sample. As such, the cuvette, or, generically, the sample container, may be made from a conductive (i.e., metal) material, which may be expensive or otherwise undesirable, such as due to the nature of the sample. Further, the sample may become contaminated due to contact with metallic surfaces. The cuvette 20 may also need to have certain characteristics that reduce the chance of electrical breakdown (e.g., arcing).

To reduce or eliminate the requirements for the sample holder 26, and in the depicted embodiment, the cuvette 20, the pulse generation system 10 may be capacitively coupled to the load 14. The system 10 may include a capacitive element 36 disposed between the pulse generating circuitry 12 and the sample 24, as illustrated in FIG. 1. In some embodiments, the capacitive element 36 may be disposed between the pulse generating circuitry 12, and the electrode 16. In the capacitively coupled system 10, the capacitive element 36 prevents direct current (DC) from flowing through the sample 24, and forces bipolar impulsive currents through the sample.

Figure 2:
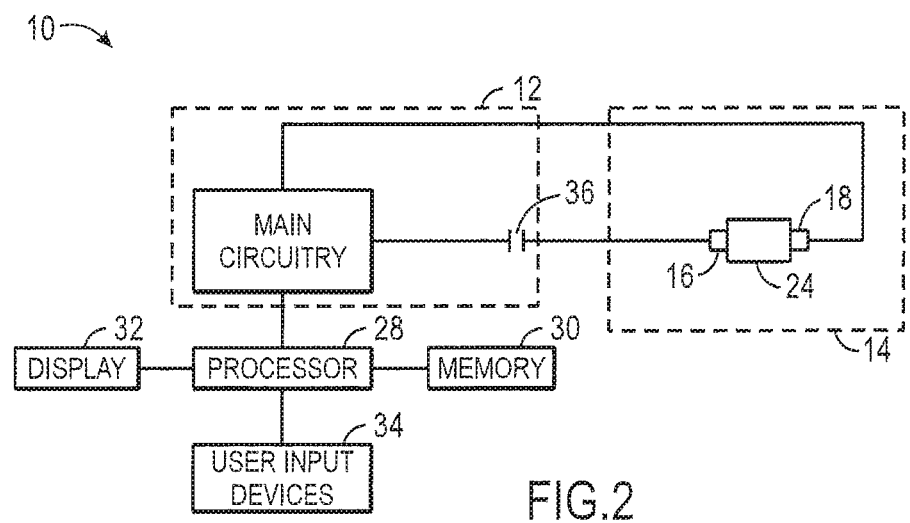
FIG. 2 is a schematic of the pulse generation system and load of FIG. 1, in accordance with an embodiment of the present approach.
Figure 3:
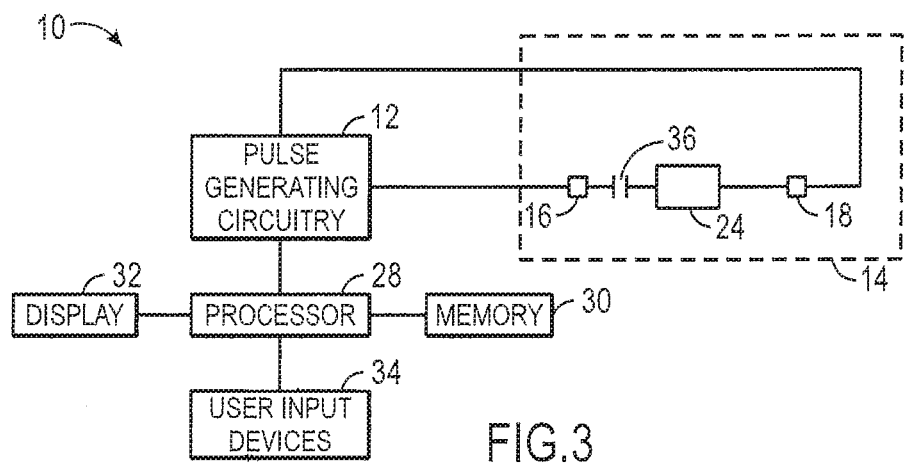
FIG. 3 is a schematic of the pulse generation system and load of FIG. 1, in accordance with another embodiment of the present approach.

The capacitive element 36 may be any suitable component or material that acts as a capacitor and is disposed in series with the sample 24. For example, the capacitive element 36 may be a capacitor disposed at the end of the pulse generating circuitry 12, as illustrated in FIG. 2. A capacitor 36 may also be disposed between the electrode 16 and the sample 24, as illustrated in FIG. 3. For example, a capacitor 36 may be attached to a compartment located between the electrode 16 and the sample holder 26 in a cuvette.

In some embodiments, the capacitive element 36 may be the cuvette 20 or generally a sample container. The cuvette 20 may be made of a nonconductive material (e.g., quartz, plastic), which allows the cuvette to act as a capacitor. Nonconductive materials may be cheaper, easier to sterilize, and less prone to contamination than conductive materials. The nonconductive materials may also be more readily available. For example, if the system 10 is used for platelet activation, then the sample holder 26 may be the syringe used to collect the sample 24 (i.e., blood).

In some embodiments, the pulse generation system 10 using capacitive coupling may be configured to generate bipolar pulses. The processor 28 may control the pulse generating circuitry 12 such that two electric pulses, one after the other, may be generated. These two electric pulses may have the same pulse duration. However, the amplitude of the electric pulses may be additive inverses. For example, the first electric pulse may have an electric field strength of 50 kV/cm, while the second electric pulse may have an electric field strength of −50 kV/cm. As will be appreciated, the first pulse may have a positive polarity and the second pulse a negative polarity or vice versa, so long as the polarity of the first pulse is opposite that of the second pulse.

Pulse generation systems using capacitive coupling may have benefits related to the results of electrically stimulating the samples. For example, in platelet activation techniques using electrical stimulation, the rate of growth factor release may vary based on the types of electric pulses emitted by a capacitively coupled pulse generation system. For instance, an electric pulse a may cause a growth factor a to be immediately released, and a growth factor b to be subsequently released. On the other hand, an electric pulse b may cause a steady rate of release for growth factor a, while halfway through the process growth factor bis released. The characteristics for the pulses associated with varying growth factor release may be determined by empirical studies. These pulse configurations may be incorporated into the protocols stored on the memory 30, or may be specified by user input.

Figure 4:
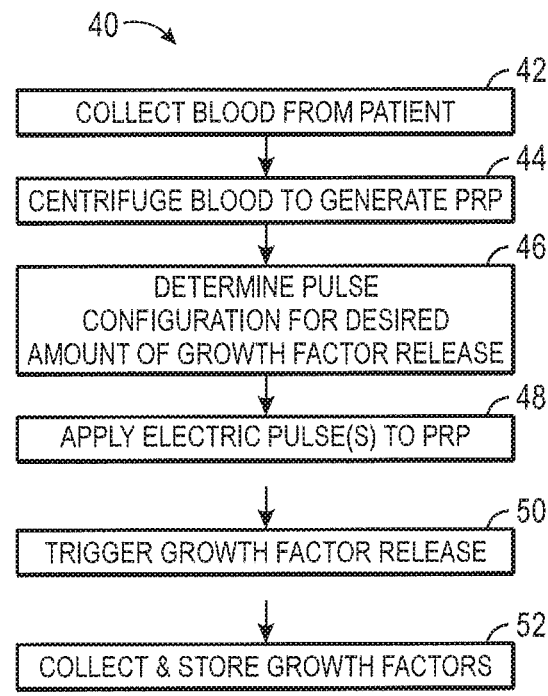
FIG. 4 is a flow chart illustrating a method for ex vivo growth factor release, in accordance with an embodiment of the present approach.

A method 40 for triggering growth factor release, as illustrated in FIG. 4, may be used in conjunction with the system 10. It should be understood that certain steps of the method 40 may be performed by an operator while other steps of the method may be performed by the system 10. At step 42, personnel (e.g., a doctor or nurse) draw blood from a patient, which is centrifuged to generate a PRP sample in step 44. In the depicted implementation, personnel determine the correct sequence and configuration of one or more pulses to apply to the PRP sample to trigger a specific amount of released growth factors in step 46. In other embodiments, personnel may determine the correct sequence of pulses based on the desired type of released growth factors and/or desired rate of release. During step 48, the PRP sample is exposed to the one or more pulses, which triggers growth factor release in step 50. Finally, in step 52, the growth factors are collected from the PRP sample.

While certain applications may benefit from capacitive coupling, others may benefit from direct coupling. As such, it may be desirable for the pulse generation system 10 to be able to couple capacitively or directly to the load 14 based on the application. For example, as mentioned above, the capacitive element 36 may be a capacitor disposed between the electrode 16 and the sample holder 26. The capacitor 36 may be removable, such that the system 10 normally uses direct coupling, and when capacitive coupling is desired the operator attaches the capacitor 36. Similarly, an operator may use a conductive sample holder 26 when direct coupling is desired and a nonconductive sample holder 26 when capacitive coupling is desired.

Figure 5:
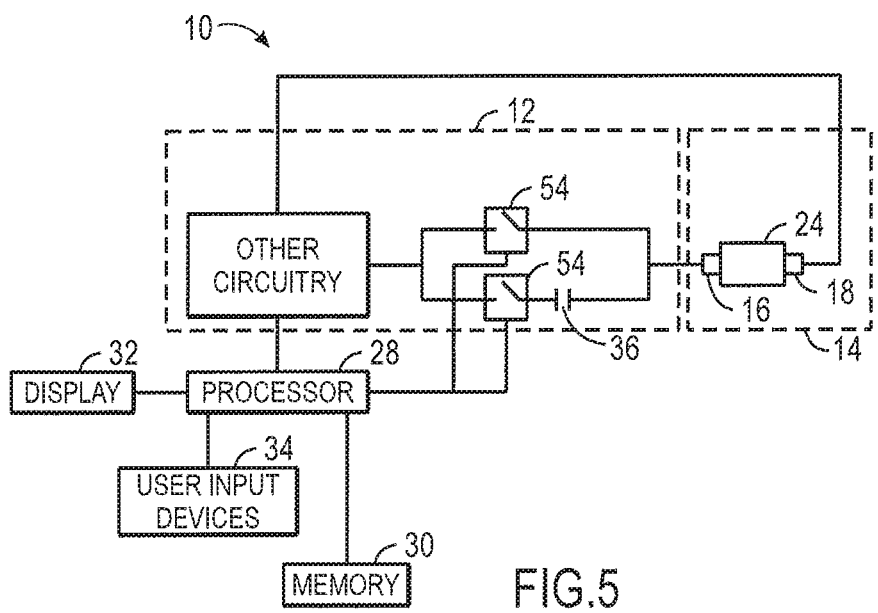
FIG. 5 is a schematic of a pulse generation system both capacitively and directly coupled to a load, in accordance with an embodiment of the present approach.

Alternatively, the pulse generating circuitry 12 may include circuitry that allows current to flow directly to the load 14 (i.e., direct coupling) or routes current through a capacitive element 36 (i.e., capacitive coupling) prior to the load 14, as illustrated in FIG. 5. For example, the pulse generating circuitry 12 may include, in parallel, a direct coupling to the load 14 and the capacitive element 36 (e.g., a capacitor) in series with the load 14 (i.e., capacitive coupling). The processor 28 may control two switches 54 that allow current to flow to the load 14 either via direct coupling or capacitive coupling. The switches 54 may be any device capable of being selectively changed between an electrically conductive state and a nonconductive state, such as silicon controlled rectifiers, power transistors, relay switches, or any other like devices. Alternatively, the processor 28 may control other devices, such as analog or digital multiplexors, that are capable of selecting the circuitry associated with the desired coupling scheme. The processor 28 may receive a user input specifying which coupling scheme the system 10 should use. The protocols stored on the memory 30 specifying the characteristics of the pulses generated may also specify whether to use direct or capacitive coupling.

Some applications may also benefit from a series of electric pulses delivered to the load 14 that alternate between direct and capacitive coupling. Such configurations may be incorporated into the protocols stored on the memory 30, or may be specified by user input.

EXAMPLES

Controlling the Amount of Growth Factor Release During Platelet Activation

Figure 6:
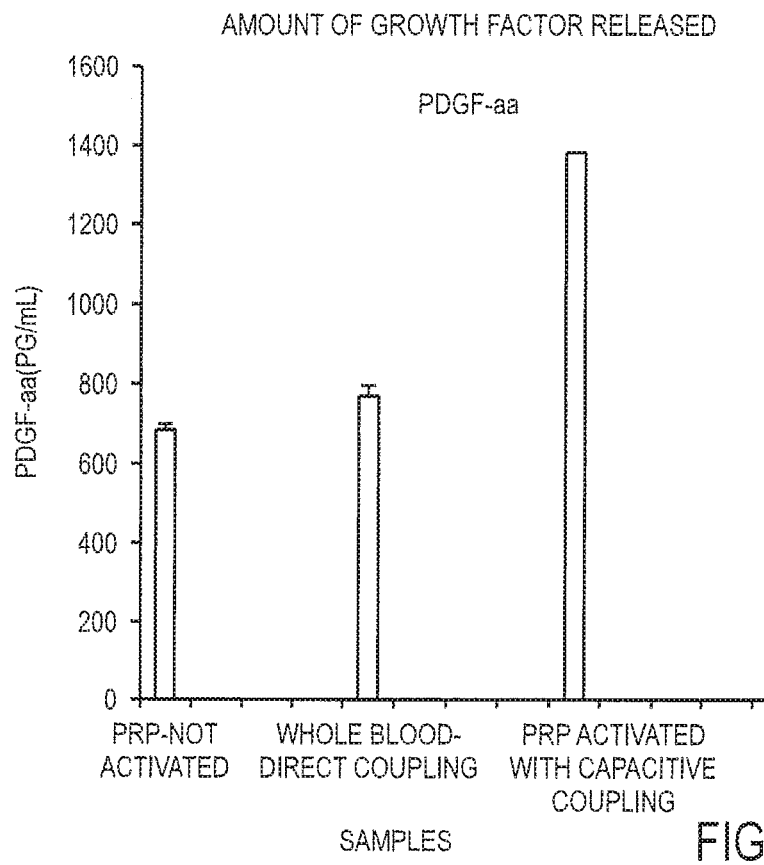
FIG. 6 is a graph displaying the amount of platelet derived growth factor released in unactivated PRP, an unactivated whole blood sample, and a PRP sample capacitively coupled to the pulse generation system.

FIG. 6 depicts the amount of growth factor release in various types of blood samples using electrical stimulation, as discussed herein, along with a capacitive coupling approach. Results are shown for samples that include a platelet rich plasma (PRP) sample that has not been activated, a whole blood sample that has not been activated, and a PRP sample that has been activated via electrical stimulation in a capacitively coupled pulse generation system. The PRP samples were exposed to bipolar pulses with a voltage of 700 V (electric field strength of 3.5 kV/cm) and a current of 30 A. As illustrated, the amount of platelet derived growth factor (PDGF) present in the capacitively coupled PRP sample is about twice that of the non-activated PRP sample and the whole blood sample.

Figure 7:
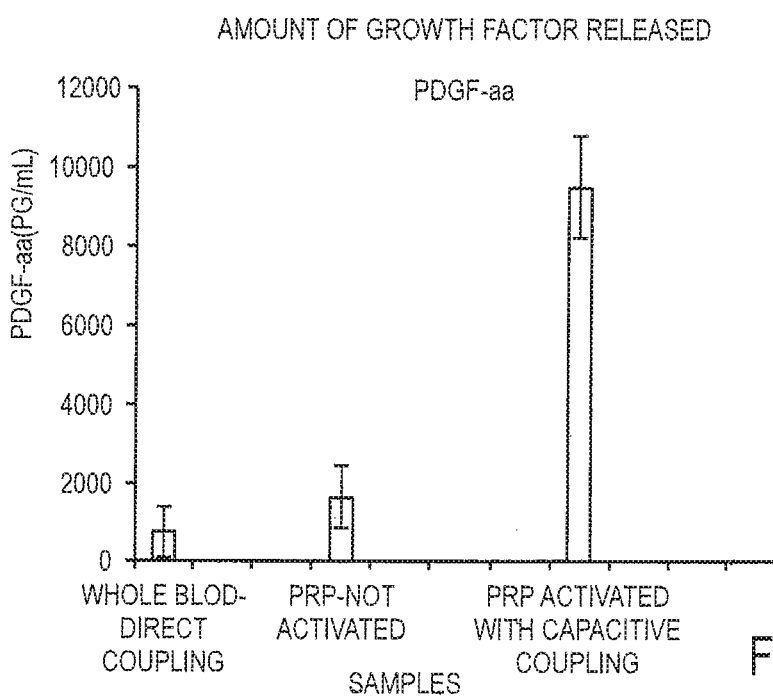
FIG. 7 is a graph displaying the amount of platelet derived growth factor released in unactivated PRP, an unactivated whole blood sample, and a PRP sample capacitively coupled to the pulse generation system.
Figure 8:
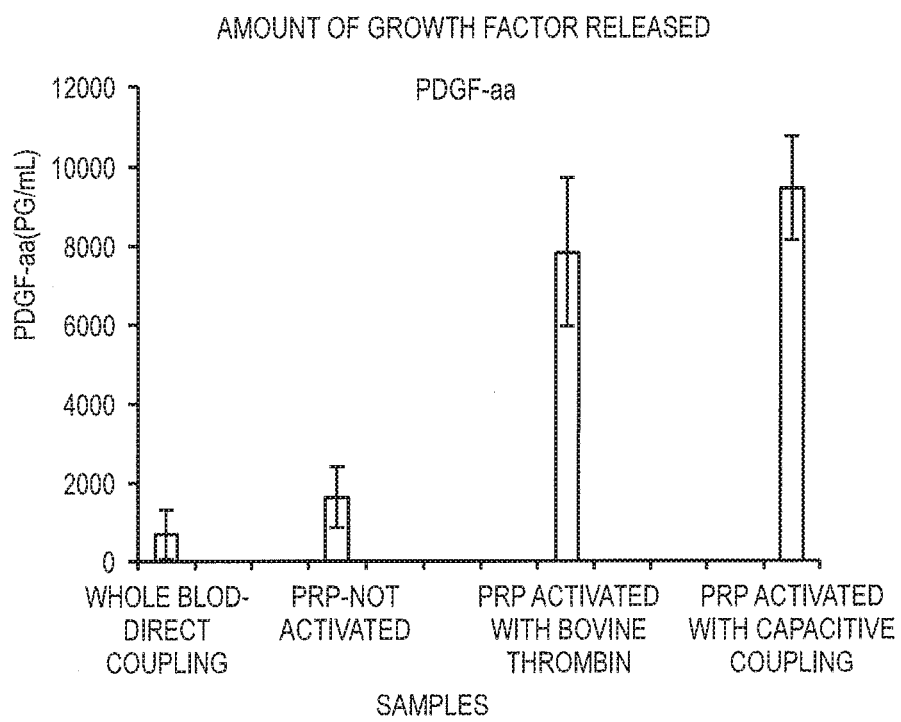
FIG. 8 is a graph displaying the amount of platelet derived growth factor released in various blood samples using various approaches, including approaches discussed herein.

FIG. 7 illustrates the amount of growth factor release in similar types of samples as in FIG. 6—but a higher capacitive coupling voltage triggers more growth factor release compared to the baseline, non-activated PRP and whole blood. Here, the capacitively coupled PRP sample was exposed to bipolar pulses with a voltage of 1200 V (electric field strength of 6 kV/cm) and a current of 60 A. The amount of PDGF released in the capacitively coupled PRP sample was six times more than that of the non-activated PRP sample and about thirteen times more than that of the whole blood sample. As shown, the voltage and current characteristics of the electrical stimulation affect the amount of growth factor released compared to the baseline when the pulse generation system is capacitively coupled to the sample. To further illustrate the effectiveness of the capacitively coupled pulse generation system, FIG. 8 compares the amount of PDGF released in a non-activated PRP sample, a whole blood sample not exposed to electrical stimulation, a blood sample activated with bovine thrombin, and a capacitively coupled PRP sample.

One or more of the disclosed embodiments, alone or in combination, may provide one or more technical effects useful for providing pulsed power in various applications. Certain embodiments may allow operators to use nonconductive materials for sample holders in pulse generation systems. For example, the present capacitively coupled pulse generation system may use a syringe or other plastic container as a sample holder. These nonconductive samples holders may be less expensive, easier to sterilize, and more readily available than sample holders used in conventional pulse generation systems. Additionally, samples that are electrically stimulated using the present capacitively coupled pulse generation system may differ based on the types of pulses used. For instance, varying the pulse parameters for the present capacitively coupled pulse generation system for platelet activation may modify the amount of growth factors released. Other embodiments may also allow operators to use direct or capacitive coupling in pulse generation systems. For example, the present pulse generation system may contain suitable control and pulse generating circuitry that allows current to flow directly to the sample (i.e., direct coupling) or reroutes the current through a capacitive element (i.e., capacitive coupling). The technical effects and technical problems in the specification are exemplary and not limiting. It should be noted that the embodiments described in the specification may have other technical effects and can solve other technical problems.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An electric pulse generation system comprising:
   a sample holder comprising two electrodes wherein the sample holder is configured to electrically couple the two electrodes to a sample container disposed in the sample holder;
   pulse generating circuitry configured to generate an electrical pulse between the two electrodes;
   control circuitry configured to cause the pulse generating circuitry to generate the electrical pulse to deliver a pulse to the sample container disposed in the sample holder; and
   a capacitor disposed in series with the pulse generating circuitry and the two electrodes during the generation of the electrical pulse between the two electrodes.

2. The electric pulse generation system of claim 1, comprising a resistive path disposed in series with the pulse generating circuitry and the two electrodes and disposed in parallel with the capacitor, and wherein the resistive path comprises a switch configured to bypass the capacitor.

3. The electric pulse generation system of claim 2, wherein the control circuitry is configured to control the switch to bypass the capacitor during the delivery of the pulse.

4. The electric pulse generation system of claim 1, wherein the capacitor is replaceable.

5. The electric pulse generation system of claim 1, wherein the sample container comprises a cuvette.

6. The electric pulse generation system of claim 1, wherein the electrical pulse comprises a duration between about 1 nanosecond and about 100 microseconds.

7. The electric pulse generation system of claim 1, wherein the electrical pulse comprises an electric field strength between 0.1 kV/cm and 350 kV/cm.

8. An electric pulse generation system comprising:
   a sample holder comprising two electrodes disposed on opposite sides of the sample holder, wherein the sample holder is configured to receive a sample container;
   pulse generating circuitry configured to supply a pulse between the electrodes;
   a first resistive path that directly couples the pulse generating circuitry and the two electrodes;
   a second resistive path that couples the pulse generating circuitry and the two electrodes through a capacitive element disposed in series with the two electrodes and the pulse generating circuitry; and
   switching circuitry configured to select between the first and the second resistive path.

9. The electric pulse generation system of claim 8, comprising:

a memory configured to store a protocol comprising a first set of instructions and a second set of instructions for the electric pulse generation system; and a processor configured to execute the protocol stored on the memory, wherein the first set of instructions causes the pulse generating circuitry to supply the pulse between the electrodes, and the second set of instructions causes the switching circuitry to select between the first and the second resistive path.

10. The electric pulse generation system of claim 9, wherein the first set of instructions comprises a pulse shape or a series of pulse.

11. The electric pulse generation system of claim 8, wherein the capacitive element comprises replaceable capacitor.

12. The electric pulse generation system of claim 8, wherein the electric pulse generation system is configured to receive an input from an user input device adjust the switching circuitry.

13. The electric pulse generation system of claim 8, wherein the switching circuitry comprises a first switch disposed in the first resistive path and a second switch disposed in the second resistive path.

14. A method to operate an electric pulse generation system, the method comprising:
placing a sample in a sample container;
placing the sample container in a sample holder comprising two electrodes, wherein the sample in the sample container is electrically coupled to the two electrodes; and
causing a pulse generating circuitry to deliver an electric pulse signal to the sample in the sample container via a circuit that comprises:
the pulse generating circuitry;
the two electrodes; and
a capacitor arranged in series with the two electrodes and the pulse generating circuitry during the delivery of the electric pulse signal.

15. The method of claim 14, wherein the electric pulse signal comprises a sequence of electric pulses, and wherein the method comprises selecting a configuration of the electric pulse signal based on a target parameter, the configuration comprising a number of electric pulses, a shape of the electric pulses, a voltage for the electric pulses, a duration for the electric pulses, or any combination thereof, and wherein the electric pulses are designed based on the capacitor coupled to the pulse generating circuitry.

16. The method of claim 15, wherein the target parameter comprises an amount of growth factor released.

17. The method of claim 14, comprising adjusting switching circuitry to bypass the capacitor and resistively couple the pulse generating circuitry to the two electrodes.

* * * * *